United States Patent
Chen et al.

(10) Patent No.: US 11,060,132 B2
(45) Date of Patent: Jul. 13, 2021

(54) MULTIPLEXED IMAGING USING STRAND DISPLACEMENT

(71) Applicant: Ultivue, Inc., Cambridge, MA (US)

(72) Inventors: Xi Chen, West Newton, MA (US); Stephanie Hennek, Medford, MA (US)

(73) Assignee: Ultivue, Inc., Cambridge, MA (US)

(*) Notice: Subject to any disclaimer, the term of this patent is extended or adjusted under 35 U.S.C. 154(b) by 160 days.

(21) Appl. No.: 16/117,194

(22) Filed: Aug. 30, 2018

(65) Prior Publication Data

US 2018/0371532 A1 Dec. 27, 2018

Related U.S. Application Data

(63) Continuation of application No. PCT/US2017/032398, filed on May 12, 2017.

(60) Provisional application No. 62/343,791, filed on May 31, 2016, provisional application No. 62/336,676, filed on May 15, 2016.

(51) Int. Cl.
| | |
|---|---|
| *C12Q 1/6806* | (2018.01) |
| *G01N 33/58* | (2006.01) |
| *C12Q 1/6855* | (2018.01) |
| *C12Q 1/6869* | (2018.01) |
| *C07K 16/00* | (2006.01) |
| *A61K 47/68* | (2017.01) |

(52) U.S. Cl.
CPC ............ *C12Q 1/6806* (2013.01); *A61K 47/68* (2017.08); *C07K 16/00* (2013.01); *C12Q 1/6855* (2013.01); *C12Q 1/6869* (2013.01); *G01N 33/58* (2013.01); *C12Q 2525/191* (2013.01); *G01N 2458/10* (2013.01)

(58) Field of Classification Search
CPC ...... C12Q 2537/1373; C12Q 2537/163; C12Q 1/6804; C12Q 2543/10; C12Q 1/6806; A61K 47/68; C07K 16/00; G01N 2458/10; G01N 33/58
See application file for complete search history.

(56) References Cited

U.S. PATENT DOCUMENTS

| | | |
|---|---|---|
| 2012/0258880 A1 | 10/2012 | Schwartz et al. |
| 2015/0152473 A1* | 6/2015 | Nadeau ............... C12Q 1/6851 506/9 |
| 2016/0002704 A1 | 1/2016 | Diehl et al. |

FOREIGN PATENT DOCUMENTS

| | | |
|---|---|---|
| WO | 2013177046 A1 | 11/2013 |
| WO | 2014028538 A2 | 2/2014 |
| WO | 2015017586 A1 | 2/2015 |

OTHER PUBLICATIONS

Zimak et al., "Programming in Situ Immunofluorescence Intensities through interchangeable Reactions of Dynamic DNA Complexes," ChemBioChem, vol. 13, pp. 2722-2728. (Year: 2012).*

(Continued)

*Primary Examiner* — Young J Kim
(74) *Attorney, Agent, or Firm* — McNeill Baur PLLC

(57) ABSTRACT

The present disclosure describes various improved methods for imaging at least one target in a sample, including methods employing an adapter strand oligonucleotide and a bridge strand oligonucleotide. Some methods also employ bouncer oligonucleotides and/or blocker oligonucleotides. Some methods also use two partial docking strands to detect proximity of the partial docking strands to each other.

7 Claims, 7 Drawing Sheets

(56) References Cited

OTHER PUBLICATIONS

Zimak et al. Supporting Information, ChemBioChem, vol. 13, pp. 1-6. (Year: 2012).*

Jungmann et al., "Multiplexed 3D cellular super-resolution imaging with DNA-PAINT and Exchange-Paint," Nature Methods 11(3):313-318 (2014).

Scheible et al., "Single Molecule Characterization of DNA Binding and Stand Displacement Reactions on Lithographic DNA Origami Microarrays," Nano Lett. 14(3):1627-1633 (2014).

Shang et al., "Multiplexed In-Cell Immunoassay for Same-Sample Protein Expression Profiling," Scientific Reports 5 (1), 13651, 12 pages (2015).

Supplementary European Search Report issued in European Application No. 17799912.5, dated Dec. 9, 2019, 11 pages.

Duose et al., "Configuring robust DNA strand displacement reactions for in situ molecular analyses," Nucleic Acid Research, 2012, 40(7):3289-3298.

Duose et al., "Multiplexed and Reiterative Fluorescence Labeling via DNA Circuitry," Bioconjugate Chem. 2010, 21, 2327-2331.

International Search Report and Written Opinion issued in International Application No. PCT/US2017/032398, dated Oct. 2, 2017, 11 pages.

Li et al., "Rational, modular adaptation of enzyme-free DNA circuits to multiple detection methods," Nucleic Acids Research, 2011, 39(16):1-13.

Schweller et al., "Multiplexed in situ Immunofluorescence via Dynamic DNA Complexes," Angew Chem Int Ed Engl. Sep. 2012, 51(37):9292-9296.

Yurke et al., "A DNA-fuelled molecular machine made of DNA," Nature 406, 605-608, Aug. 2000.

Yurke et al., "Using DNA to Power Nanostructures," Genetic Programming and Evolvable Machines, 4, 111-122, 2003.

Zhang et al., "Engineering Entropy-Driven Reactions and Networks Catalyzed by DNA," Science 318, 1121-1125 (2007).

Zimak et al., "Programming in situ immunofluorescence intensities through interchangeable reactions of dynamic DNA complexes," Chembiochem. Dec. 2012, 13(18):2722-2728.

* cited by examiner

MULTIPLEXED IMAGING USING STRAND DISPLACEMENT

CROSS-REFERENCE TO RELATED APPLICATIONS

This application is a continuation of International Application No. PCT/US2017/032398 filed May 12, 2017, and claims the benefit of priority of U.S. Provisional Application Nos. 62/336,676, filed May 15, 2016, and 62/343,791, filed May 31, 2016, the contents of all of which are incorporated by reference herein in their entirety for any purpose.

DETAILED DESCRIPTION

Field

Improved Multiplex Imaging of Targets in a Sample Employing Strand Displacement.

Background

DNA strand displacement is a method for the isothermal and dynamic exchange of DNA complexes.[1-3] Strand displacement can be designed and intentionally controlled based on an understanding of DNA hybridization interactions and thermodynamics, and can be facilitated by introducing engineered handles which are known as "toehold domains." The ability to modulate binding interactions and exchange hybridization partners gives rise to a series of potential applications. Several of these applications have been proposed and demonstrated by Diehl and coworkers,[4-7] including multiplexed protein detection and signal amplification applications in fixed cells using immunofluorescence microscopy.

The current state of the art as proposed by Diehl and coworkers provides only a narrow implementation of strand displacement for fluorescence microscopy. The design proposed by Diehl and coworkers can be costly since it requires conjugation of distinct nucleic acid sequences to each target-recognition element in the assay. The efficiency of strand displacement is not optimal, and may induce unwanted non-specific binding due to the use of longer DNA strands.

Here we propose several new, unanticipated embodiments based on DNA strand displacement.

SUMMARY

In accordance with the description, a method for imaging of at least one target in a sample comprises: (a) providing at least one target-recognizing antibody bound to an adapter strand oligonucleotide; (b) providing a bridge strand oligonucleotide with a region capable of specifically binding the adapter strand oligonucleotide and a docking strand region; and (c) providing an imager strand oligonucleotide capable of specifically binding the docking strand region of the bridge strand oligonucleotide, wherein the imager strand is labeled with a detectable label.

In some embodiments, a method for imaging of at least one target in a sample comprises (a) providing at least one target-recognizing antibody bound to a docking strand oligonucleotide; (b) providing a blocker strand that hybridizes to the docking strand over a first region, but not over its full length or the full length of the docking strand; (c) providing an imager strand oligonucleotide that hybridizes to the docking strand oligonucleotide at least in the region of the docking strand that does not hybridize to the blocker strand, wherein the imager strand is labeled with a detectable label; (d) allowing the imager strand to hybridize to the docking strand, displacing the blocker strand; (e) determining whether the target-recognizing antibody has bound to the target.

In some embodiments, a method for imaging of at least two target in a sample comprises (a) providing at least two target-recognizing antibodies bound to a docking strand oligonucleotide; (b) providing a first imager strand oligonucleotide capable of hybridizing to the docking strand on the first target-recognizing antibody and providing a first blocking strand capable of hybridizing to the docking strand on the second target-recognizing antibody, wherein the imager strand is labeled with a detectable label and the blocking strand is not labeled with a detectable label and wherein optionally additional blocking strands are used if more than two target-recognizing antibodies are present; (c) imaging the first target and removing the imager strand and blocking strand with at least one bouncer strand; (d) providing a second imager strand oligonucleotide capable of hybridizing to the docking strand on the second target-recognizing antibody and providing a second blocking strand capable of hybridizing to the docking strand on the first target-recognizing antibody, wherein the imager strand is labeled with a detectable label and the blocking strand is not labeled with a detectable label and wherein optionally additional blocking strands are used if more than two target-recognizing antibodies are present; (e) imaging the second target; and (f) optionally removing the imager strand and blocking strand with at least one bouncer strand and optionally repeating the imaging for any additional targets.

In some embodiments, a method for imaging of at least one target in a sample comprises: (a) providing at least one first target-recognizing antibody bound to a first docking strand oligonucleotide; (b) providing at least one second target-recognizing antibody bound to a second docking strand oligonucleotide; (c) providing an imager strand oligonucleotide capable of specifically binding to the first docking strand oligonucleotide and the second docking strand oligonucleotide when the first docking strand oligonucleotide and the second docking strand oligonucleotide are in proximity to each other forming a full-length docking strand, wherein the imager strand does not specifically bind either the first or second docking strand oligonucleotide alone; (d) detecting the imager strand, wherein the imager strand is labeled.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 4A shows three primary antibodies bound to their three respective targets and having three docking strands. In FIG. 4B, the sample is treated with fluorescent-labeled imager strand 210, complementary to docking strand 207. Unlabeled blocker strand 211 and 212, complementary to docking strands 208 and 209, respectively, are added, before washing and imaging of target 204. Between the views shown in FIGS. 4B and 4C, a mixture of bouncer strands complementary to the imager or blocker strands 210, 211, and 212 are added to remove these strands. FIG. 4D shows imaging of target 205 using fluorescently-labeled imager strand 214 and blocker strands for the other docking strands.

DESCRIPTION OF THE EMBODIMENTS

I. Definitions

Docking strands are defined as oligonucleotides which are attached to targets of interest, in some embodiments, through an intermediate molecule (e.g., antibody including full length antibodies and antigen binding fragments thereof) to form a nucleic acid-target recognition complex. A docking site is defined as a region of complementarity or specific binding affinity between the docking strand and the imager strand.

Imager strands are defined as oligonucleotides attached to a label (e.g., fluorophore, nanoparticle, etc.). Blocker strands are defined as oligonucleotides with regions of complementarity to docking strands that, when bound to a docking strand, block association with any off-target imager strands; blocker strands likewise can be oligonucleotides with regions of complementarity to imager strands that, when bound to an imager strand, block association with any off-target docking strands (see FIG. 2). Bouncer strands are defined as oligonucleotides with regions of complementarity to blocker or imager strands that result in strand displacement of blocker or imager strands that are bound to docking strands.

When hybridization or hybridization conditions are referenced throughout the application, high ionic strength buffer conditions (e.g. 1× saline sodium citrate buffer, or 150 mM, 200 mM, 300 mM, 400 mM, 500 mM, or 600 mM sodium chloride in phosphate buffer) may be employed at room temperature to ensure hybridization occurs.

II. Universal Reagents to Link the Docking Strand to the Target

The Docking Strand is usually linked to the target via a target-recognizing molecule such as an antibody (including antigen binding fragments thereof) or an aptamer. Antibody is a popular type of target-recognizing molecule. Many antibody-DNA conjugation methods have been described in the past, including ones only involving covalent bonds and ones involving non-covalent bonds. Examples of conjugation methods involving non-covalent bonds include ones involving naturally occurring and engineered antibody-binding proteins, such as Protein A, Protein G and Protein A/G, as well as secondary antibodies and antibody fragments (e.g. Fab, Fab', F(ab')$_2$) that recognize the constant region/domains (e.g., Fc, CH1, CH2, CH3, CL domains).

Figure 1:
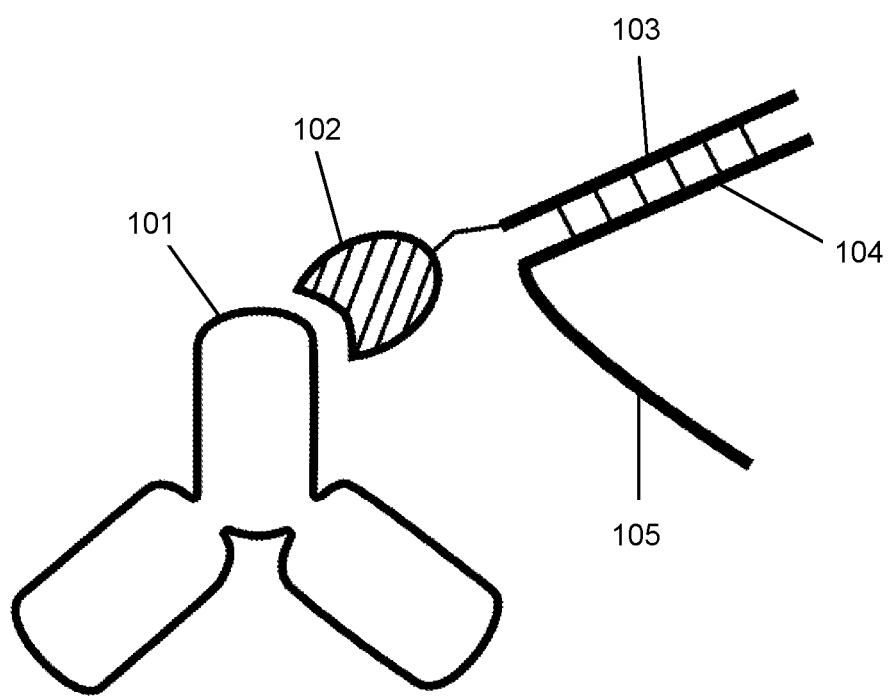
FIG. 1 shows the use of a universal reagent to link the docking strand to the target. 101 represents an antibody capable of binding to the target. The combination of 102 and 103 represent a universal adaptor, wherein 102 is an antibody binder and 103 is a universal adapter. The combination of 104-105 represent a bridge strand with a domain that is complementary to the universal adaptor (103) and a docking site (105).

To simply the procedure in attaching different Docking Strands (of different sequences) to different target-recognizing molecules (e.g., antibodies) we here describe the use of one or a few universal adaptors. As shown in FIG. 1, one may conjugate a DNA strand with a 'universal' (i.e., target-independent) adaptor sequence (103) to an antibody binder (102) that can bind a constant region/domain of primary antibody (101). The antibody binder (102) can be Protein A, Protein G, or the like, or monovalent Fab, Fab', or the like.13 Such universal adaptor (comprising 102 and 103) can be complexed with the primary antibody by simple incubation. With or without purification, one can then add a 'bridge strand' to the complex. The bridge strand comprises two domains: one (104) complementary to the universal adaptor (103), and the other (105) serving as the docking site. The new, three-part complex can be used with or without purification. Optionally, one may add to the complex scavenger molecules that inactivate universal adaptor or bridge strand in excess to prevent unwanted interactions. For example, if the primary antibody is I derived from mouse, one may use normal mouse IgG (or normal mouse serum) to quench the excess universal adaptor (102-103) so that the universal adaptor does not bind other mouse primary antibodies that may be present in the sample. For another example, one may use stand-alone DNA strand 103 to quench the excess bridge strand (104-105) so that the bridge strand does not bind universal adaptor strand bound to other targets.

One may also exercise part of this concept. For example, one may covalently conjugate the universal adaptor sequence (103) to the primary antibody (instead of using the antibody-binder, 102) to get the benefit of not having to chemically conjugate different DNA sequences to the antibody if, for example, the sequence of the docking site needs to be optimized.

III. Use of Direct Hybridization to Introduce Imager Strand

In the demonstration of Diehl and colleagues, the Imager Strand is introduced to the sample (which contains the Docking Strand as a single-stranded DNA) as a part of a duplex that also contains a 'protector' strand with sequence complementary to the Imager Strand. The protector strand 'shields' some bases on the Imager Strand and may prevent it from interacting with non-target molecules via unwanted Watson-Crick pairing or other nonspecific interactions. However, this design requires that the Imager Strand is long. To be specific, in the prior design, the portion of the Imager Strand that is complementary to the docking site has to be long because it must contain two domains: (a) a single-stranded toehold domain that initiates the interaction with the docking site, and (b) a domain that is bound to the protector strand. The toehold of (a) must be at least ~5-nt-long (assuming ~50% GC content) to initiate fast strand displacement, and the protector-bound domain of (b) must be at least ~12-nt-long (assuming ~50% GC content) to ensure stable hybridization. Therefore, in the prior design, the total length of the portion of the Imager Strand that is complementary to the docking site has to be at least ~17-nt (assuming ~50% GC content). As a result, in the prior design, the docking site also has to be at least ~17-nt (assuming ~50% GC content).

In our new design, the Imager Strand can be introduced as a single-stranded DNA without the protector strand. In this design, the length requirement of the portion of the Imager Strand that is complementary to the docking site is long enough to ensure stable hybridization with the Docking Strand, in some embodiments with the minimum length being ~12-nt (assuming ~50% GC content). The docking site can also be of similar length. The shorter length can make the design more compact and reduce the chance of DNA-induced non-specific binding.

IV. Use Other Dynamic Complex to Introduce and Remove Imager Strand

A standard way to carry out toehold-mediated strand-displacement is to use 3-way branch migration involving a common strand, an incumbent strand, and an invading strand. An example of this process is shown in the 'label' reaction of FIG. 2A of US2016/0002704 A1, where the fluorescent-labeled strand is the common strand, the 'waste' strand is the incumbent strand, and the NA tag is the invading strand. A drawback of 3-way branch migration is that the invading strand must be single-stranded. Such a long (at least ~17-nt as described before) single-stranded DNA may cause unwanted non-specific binding.

Figure 2:
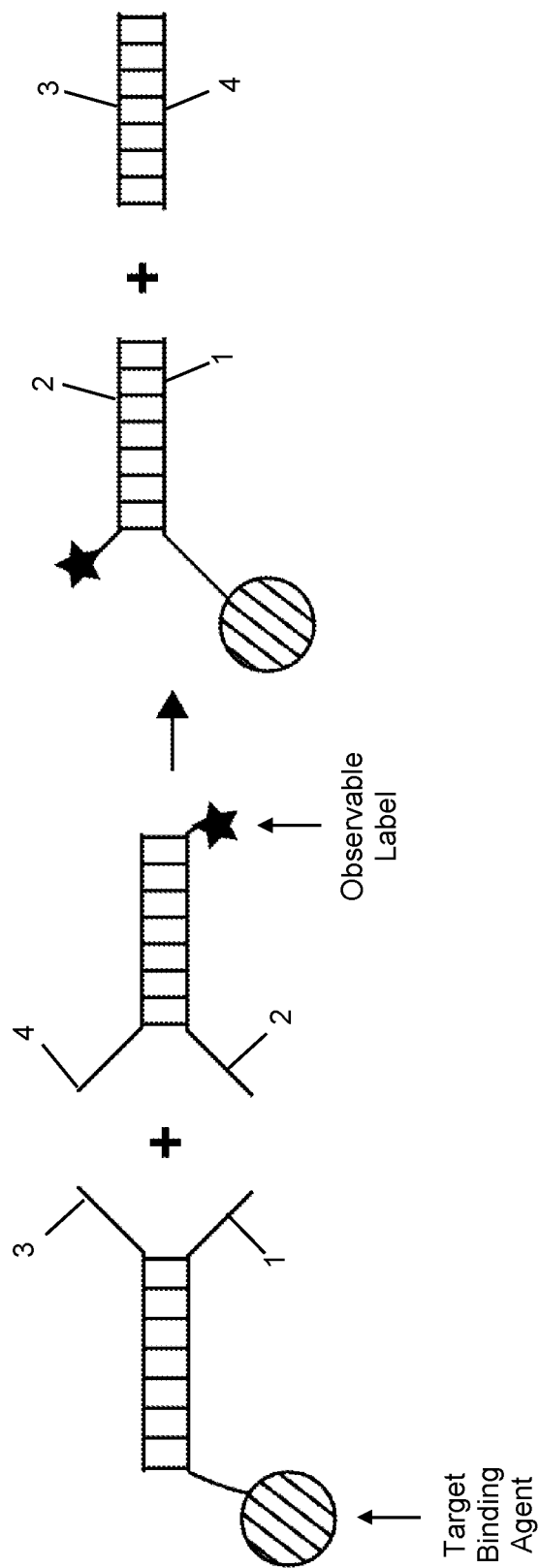
FIG. 2 illustrates the use of a dynamic complex to introduce and remove imager strand using 4-way branch migration. The target binding agent of FIG. 2 may be an antibody in some embodiments.

As a new approach, to reduce the length of single-stranded DNA one may use 4-way branch migration to introduce and remove the Imager Strand. One example is shown in FIG. 2. FIG. 2 shows a docking strand attached to a target-recognizing antibody with a docking strand 1 which hybridizes over part of its length to a blocker strand 3 and over at least some of the remaining length to imager strand 2 with an observable label. Imager strand 2 also hybridizes over part of its length to a blocker strand 4. This allows imager strand 2 to replace blocker strand 3. Optionally, blocker strand 3 and blocker strand 4 hybridize to each other over their full length. This embodiment shows both blocker strands to docking strands and blocker strands to imager strands.

Figure 3:
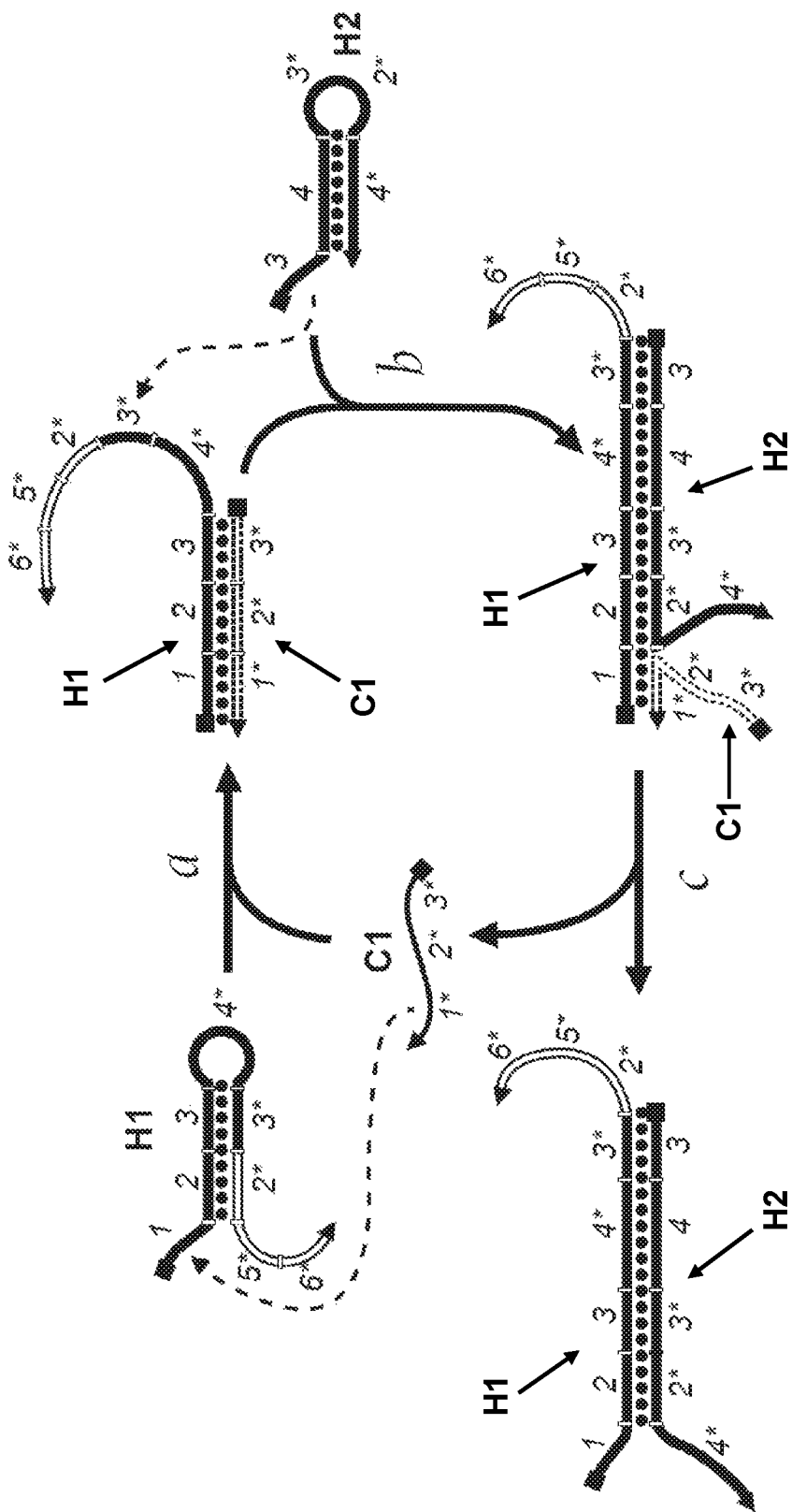
FIG. 3 illustrates one reaction (a) to introduce the imager strand and the reaction (b and c) to remove it from the docking strand.
Figure 4A:
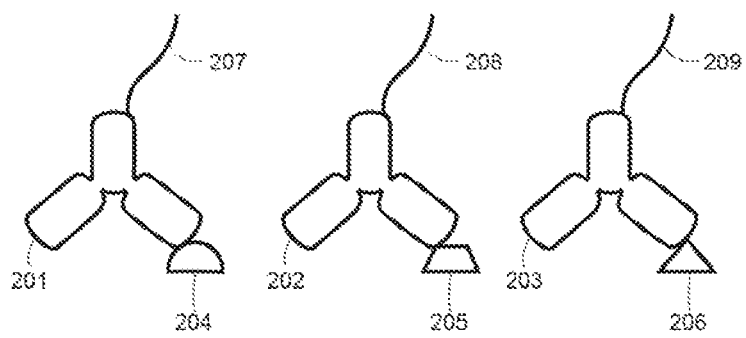
FIGS. 4A-D shows various embodiments of the use of blocker strands.
Figure 4B:
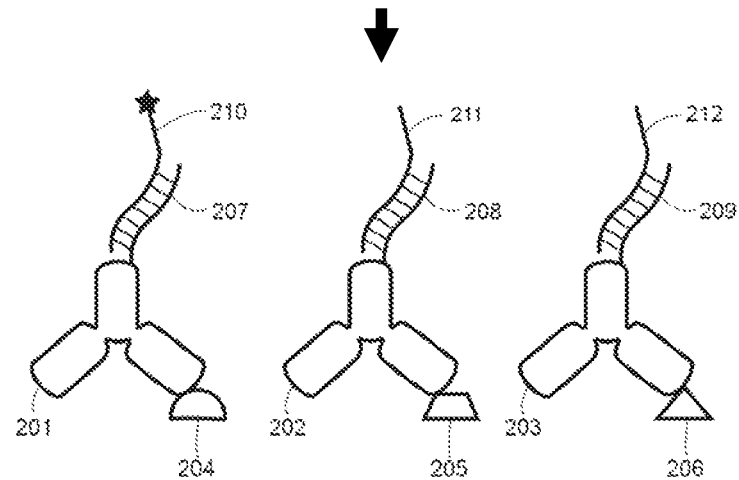
Figure 4C:
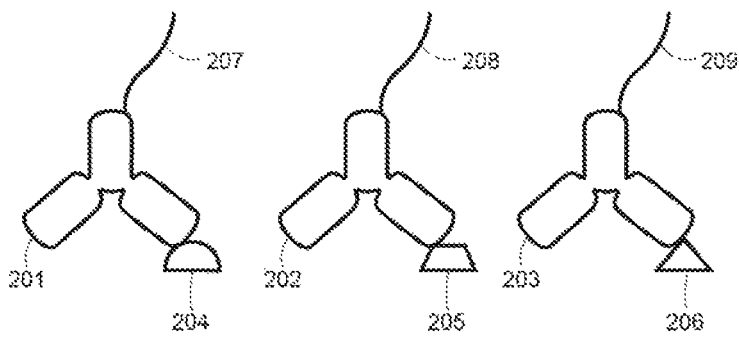
Figure 4D:
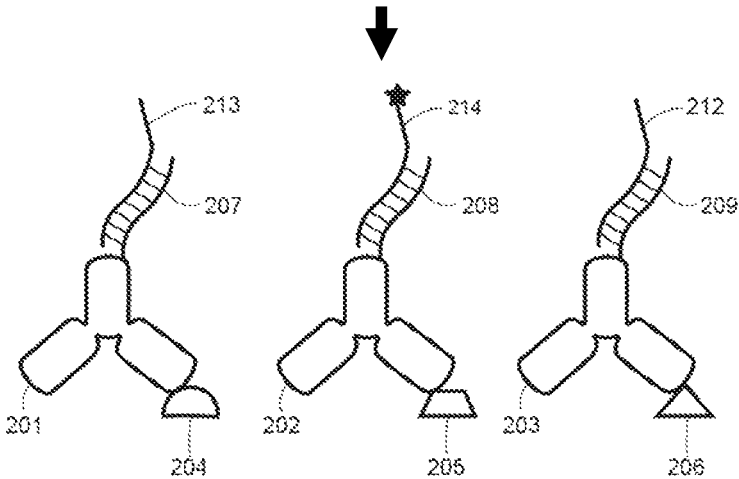
Figure 5:
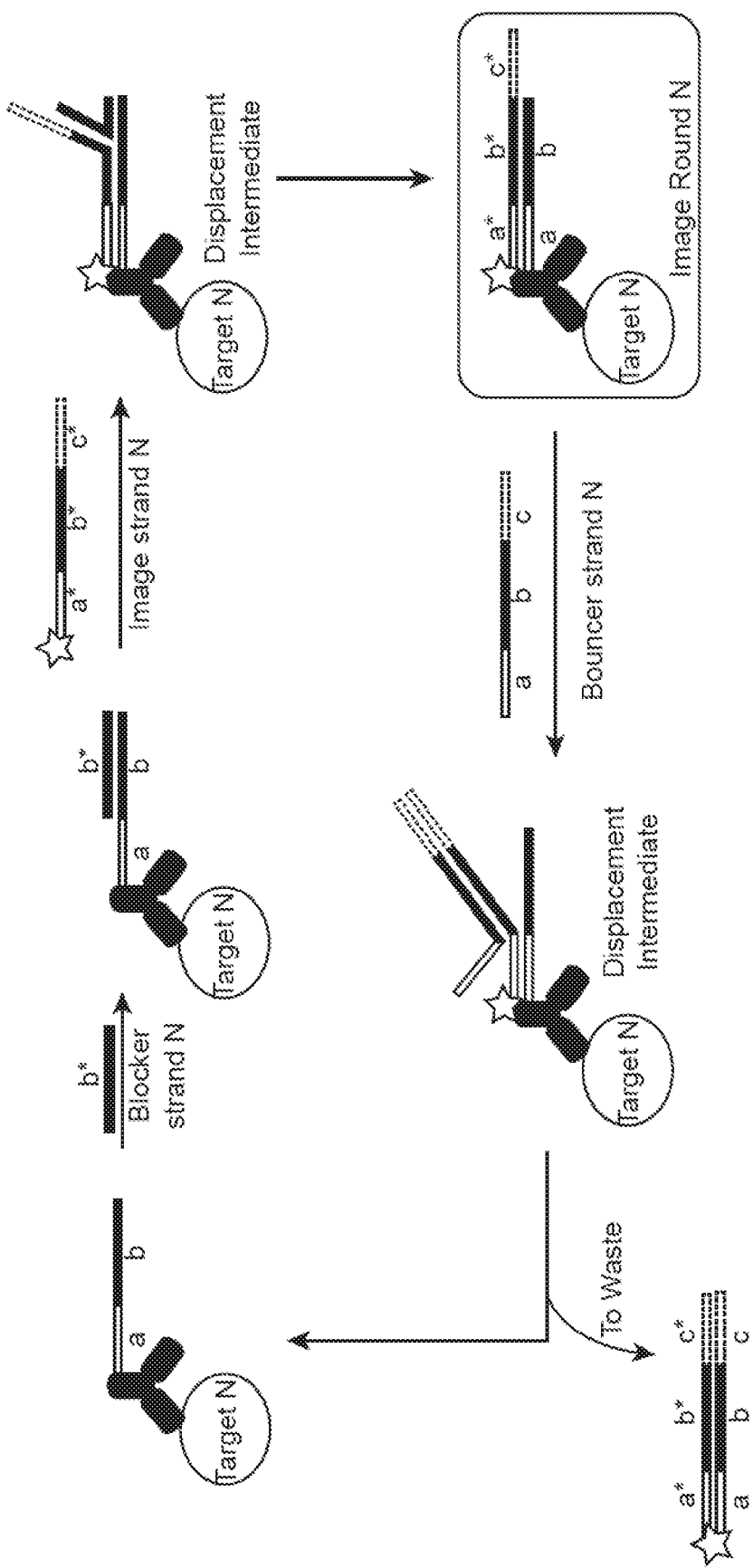
FIG. 5 illustrates exchange imaging using blocker and bouncer strands. Binding domains are labeled by letters and letters with asterisks to indicate complementary pairs (e.g. domain a hybridizes to domain a*). First, all targets are stained with nucleic acid-target recognition complexes, where the docking strand may contain two domains (e.g., a and b). Blocker strands for all targets can be introduced, where each blocker strand is complementary to at least one domain of a docking strand (e.g., b*). Then, imager strands for the target(s) being imaged can be introduced and will displace the blocker strand only for the target(s) to be imaged in the current imaging round. After acquiring images, the bouncer strand containing domains complementary to the imager strands (e.g. a, b, and c) are introduced to displace and wash away the imager strands. This cycle can be repeated for additional rounds of imaging of other targets for sequential multiplexing.

Another way to simplify the DNA constructs is to use hairpins. For example, one may use the reaction (a) of FIG. 3 to introduce the Imager Strand (implemented by H1) and use the reaction (b and c) to remove it from the Docking Strand (implemented by C1). FIG. 3 is adapted from Nucl. Acids Res. (2011) 39 (16): e110.

V. Other Forms of Signal Amplification

One may replace the fluorophore (that is brought to the target via the DNA complexes), by other molecule or moieties that can be directly or indirectly observed. These molecules or moieties include, but are not limited to, metal particles, plasmonic enhancers, enzymes (e.g., HRP), primer, capture oligonucleotide or splint of rolling circle amplification, initiator of finite or infinite hybridization chain reaction, etc.

VI. Use of Blocker Strands and Universal/Automated Exchange

A. Blocker Strands

Multiplexed imaging can be carried out with efficient exchange (e.g. via strand displacement) of imager strands from one imaging round to the next. For example, one may image the first target with the first imager strand, then displace the first imager strand with a washing step, then introduce a second imager strand to image a second target, and so on. One aspect is the addition of blocker strands for any targets that are not actively being imaged in order to reduce cross-reactivity and prevent imager strands binding to off-target docking strands. Blocker strands must be specific to one or more domain(s) of the docking strand, which is complexed to a specific target through a target-recognition entity. In one embodiment, the blocker strand is bound to a portion of the docking strand such that a toehold domain that is complementary to the imager strand remains unhybridized. Using this composition, an imager strand that is complementary to multiple domains of the docking strand including, but not limited to the toehold domain, can be introduced to displace the blocker strand prior to imaging the target. In another aspect, a bouncer strand can be introduced to strip the imager strand off of the docking strand. FIGS. 4A-D and FIG. 5 demonstrate embodiments of the components and methods used for multiplexed imaging with the addition of blocker and bouncer strands for exchange.

One embodiment is a method for universal exchange of imager strands and replacement of blocker strands to streamline sequential rounds of imaging. In one method, one or more targets are detected with one or more rounds of imaging wherein a cocktail of all bouncer strands or all blocker strands are introduced as intermediary steps between imaging rounds. A composition involving a mixture of all types of bouncer strands is contemplated as a washing buffer to displace any bound imager strands. A composition involving a mixture of all types of blocker strands is contemplated as an additive step prior to the addition of any imager strands. This composition could be part of a kit. This method could be manual, or partially or fully automated. Fluidics could be incorporated for liquid handling. Software could be incorporated for image acquisition and analysis. This method could be applied to immunohistochemistry and immunofluorescence on cell or tissue samples.

Another way to achieve similarly simplified workflow and reduce cross hybridization among DNA species is to use mixtures comprising Imager Strand(s) and Blocker Strand(s). Specifically, to image one target, one can mix the Imager Strand for this target and the Blocker Strands for all other target and apply them to the sample containing all Docking Strands. Even if the Imager Strand incorrectly binds to the Docking Strand on a wrong target, it can be displaced by the Blocker Strand for that target. One example is shown FIG. 4D. In this example we suppose there are 3 primary antibodies (201, 202, 203) that are bound to 3 targets (204, 205, 206), and are attached with 3 Docking Strands (207, 208, 209), respectively. After staining the sample with 3 DNA-attached antibodies (Stage A), one can add a mixture of (i) fluorescent-labeled Imager Strand 210, which is complementary to Docking Strand 207, (ii) unlabeled Blocker Strand 211, which is complementary to Docking Strand 208, and (iii) unlabeled Blocker Strand 212, which is complementary to Docking Strand 209. After washing one can image target 204 (Stage B). Next, one can add a mixture of Bouncer strands that are complementary to Imager/Blocker Strands 210, 211 and 212 to remove these strands from the sample (Stage C). Next, one can add a mixture of (i) unlabeled Blocker Strand 213, which is complementary to Docking Strand 207, (ii) fluorescent-labeled Imager Strand 214, which is complementary to Docking Strand 208, and (iii) unlabeled Blocker Strand 212, which is complementary to Docking Strand 209. After washing one can image target 205 (Stage D). One can use a similar process visualize target 206.

B. Use of Semi-Universal or Universal Blocker Strands

A composition for a semi-universal blocker strand is described. Such a semi-universal blocker strand may contain one domain that is universal (i.e. constant across all docking strands complexed to all targets) and one domain that is target specific.

A composition for a universal bouncer strand is described. A universal bouncer strand reduces the complexity of finding unique sequences to pair with each type of docking strand; and thus, may facilitate ultra-high multiplexing. In one embodiment, the universal bouncer strand is composed of one domain that binds to a region of a docking strand that is held constant for all target complexes. Binding of the universal bouncer strand may occur through toehold mediated strand displacement and may displace a semi-universal blocker strand.

Figure 6:
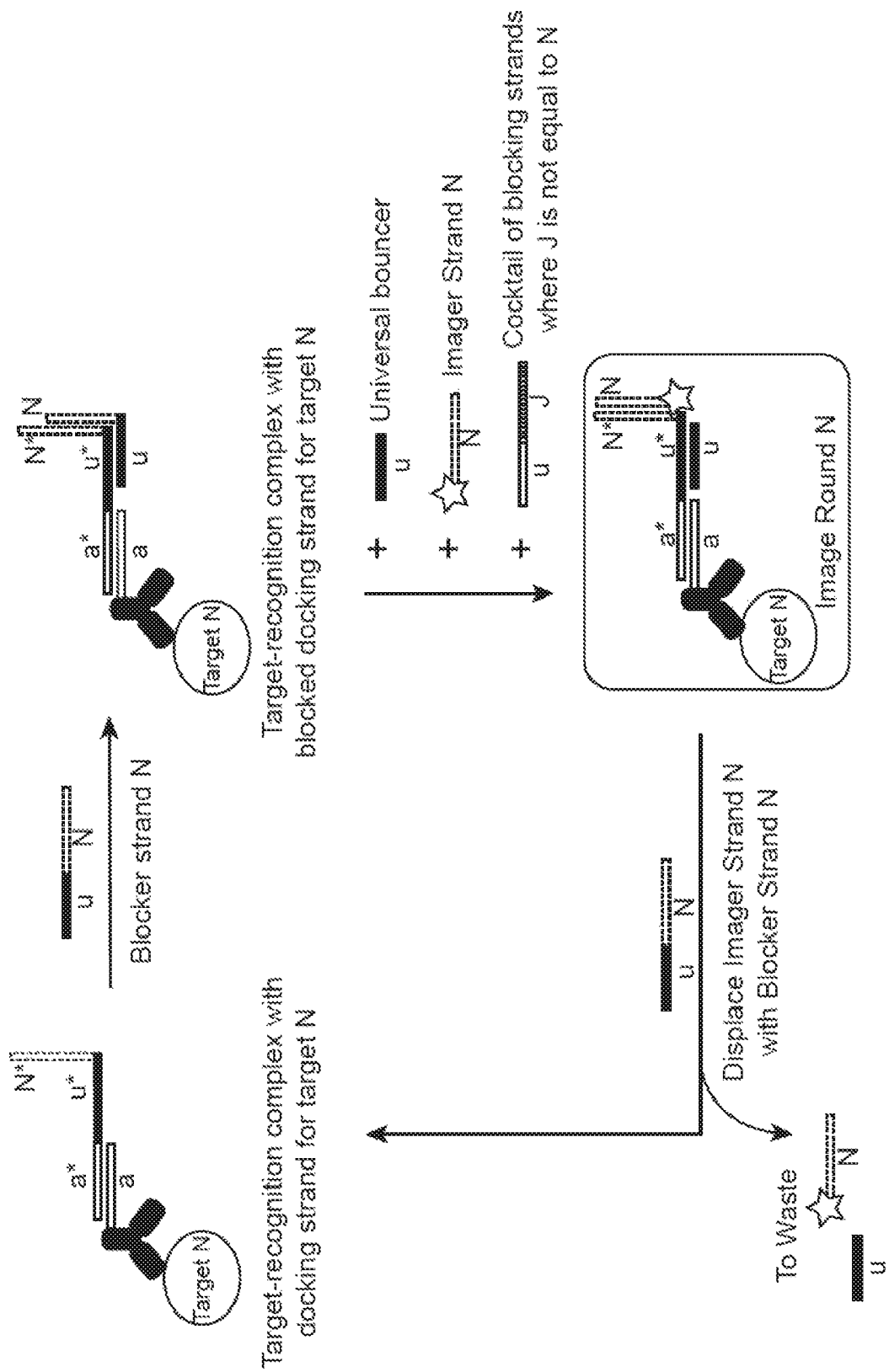
FIG. 6 shows exchange imaging using semi-universal blocker and universal bouncer strands.

A method for reiterative imaging and sequential multiplexing with semi-universal blocker strands and universal bouncer strands is described (FIG. 6). First, all targets are stained nucleic acid-target recognition complexes, where the complex includes a docking strand that may contain a constant domain (in FIG. 6 labeled as u*) and a target-specific domain (in FIG. 6 labeled as N* for the Nth target). Semi-universal blocker strands (e.g. composed of a constant domain u, and a target specific domain N) for all targets can be added and bind to the constant and target-specific domains of a docking strand. Then, a mixture can be added containing the universal bouncer strands, imager strand for the Nth target, and all semi-universal blocker strands excluding any containing a domain specific to the Nth target. During this step, the universal bouncer binds to a toehold available in the constant region of the docking strand and begins to displace the blocker strand. The imager strand binds to a toehold available in domain N* of the docking strand to complete the displacement of the blocker strand. The cocktail of semi-universal blocker strands for all other targets is added to ensure those targets remain blocked. Then, image acquisition can be carried out to detect the Nth target. Once image acquisition is complete, a mixture of all semi-universal blocker strands, including a blocker strand specific to the Nth target, can be used to displace all imager strands and universal bouncer strands prior to the next cycle or round of imaging. This cycle can be repeated for additional rounds of imaging of other targets for sequential multiplexing. It must be appreciated that the thermodynamics of each binding pair must be precisely understood, and the equilibrium for each forward reaction precisely controlled to facilitate a method involving a universal bouncer strand and semi-universal blocker strand.

VII. Proximity Detection

In another embodiment, a method of multiplexed proximity detection is proposed. Proximity detection is accomplished using a pair of nucleic acid-target recognition complexes, each of which contain a domain corresponding to a partial (such as a half of a) docking site for an imager strand. When the pair of nucleic acid-target recognition complexes are in proximity to each other, the full docking site is formed allowing an imager or blocker strand to bind. The distance between target-recognition complexes can vary based on the design of the docking strand, which can vary in length from 8, 9, 10, 11, 12, 13, 14, 15, 16, 17, 18, 19, 20, 25, 30, 50, 100 or more nucleotides. Proximity detection can be designed for distance lengths of 5 nm, 10 nm, 15 nm, 20 nm, 30 nm, 50 nm, 100 nm, or more. High ionic strength buffer conditions (e.g. 1× saline sodium citrate buffer, or 150 mM, 200 mM, 300 mM, 400 mM, 500 mM, or 600 mM sodium chloride in phosphate buffer) may be employed at room temperature to ensure hybridization occurs. The pair of nucleic acid-target recognition complexes can be designed to bind to a signal molecular target or two separate targets. An imager strand may contain two domains, one domain complementary to the full docking site, and one domain that serves as a toehold for strand displacement.

Figure 7:
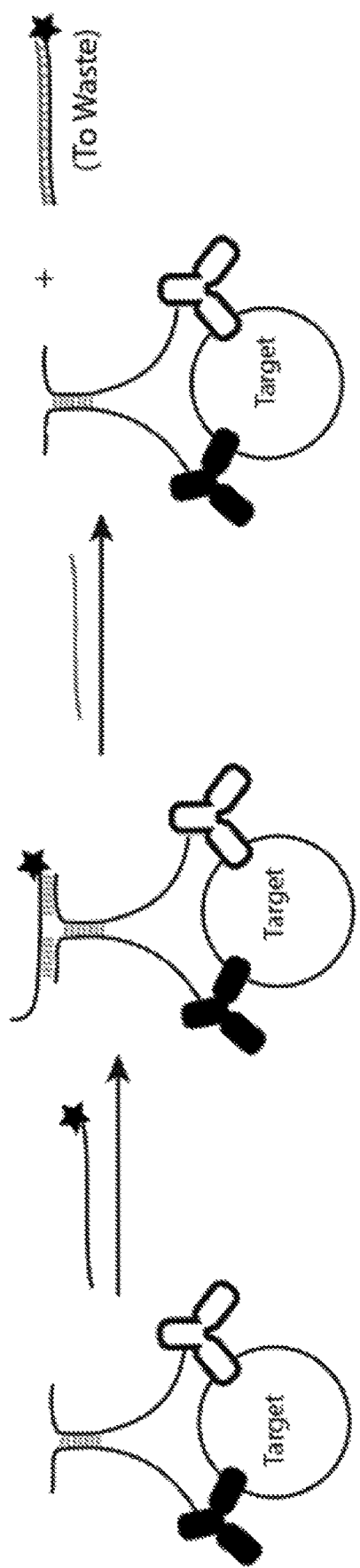
FIG. 7 provides a method for multiplexed proximity detection with strand displacement of imager strands.

For example, in FIG. 7, a target is bound with two DNA-conjugated antibodies that bind to different epitopes on the same target, bringing the DNA strands in proximity to form the full docking site. When the corresponding imager strand is added, the imager strand will bind to the full docking site, and the target can be imaged (e.g. with epi-fluorescence, confocal microscopy, TIRF, etc.). To extinguish the imaging signal, the imager strand can be displaced by the addition of a bouncer strand which binds to a toehold on the imager strand. Multiplexed proximity detection of multiple targets can be carried out with one or more rounds of strand displacement.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

REFERENCES

1. Yurke, B. & Mills, A. Using DNA to Power Nanostructures. 111-122 (2003).

2. Yurke, B., Turber, A. J., Jr, A. P. M., Simmel, F. C. & Neumann, J. L. A DNA-fuelled molecular machine made of DNA. 406, 605-608 (2000).

3. Zhang, D. Y., Turberfield, A., Yurke, B. & Winfree, E. Engineering Entropy-Driven Reactions and Networks Catalyzed by DNA. *Science* (80-). 318, 1121 (2007).

4. Duose, D. Y., Schweller, R. M., Hittelman, W. N. & Diehl, M. R. Multiplexed and Reiterative Fluorescence Labeling via DNA Circuitry. *Bioconjug. Chem.* 21, 2327-2331 (2010).

5. Duose, D. Y. et al. Configuring robust DNA strand displacement reactions for in situ molecular analyses. 40, 3289-3298 (2012).

6. Schweller, R. M. et al. Multiplexed In Situ Immunofluorescence Using Dynamic DNA Complexes. *Angew. Chemie Int. Ed.* 51, 9292-9296 (2012).

7. Zimak, J., Schweller, R. M., Duose, D. Y., Hittelman, W. N. & Diehl, M. R. Programming in Situ Immunofluorescence Intensities through Interchangeable Reactions of Dynamic DNA Complexes. 77054, 2722-2728 (2012).

What is claimed is:

1. A method for imaging of at least one target in a sample comprising:
   (a) providing at least one target-recognizing antibody directly bound to a docking strand, wherein the docking strand is a single-stranded nucleic acid;
   (b) providing a first blocker strand that hybridizes to the docking strand over a first region, but not over its full length;
   (c) providing an imager strand that hybridizes to the docking strand at least in the region of the docking strand that does not hybridize to the blocker strand, wherein the imager strand is labeled with a detectable label;
   (d) allowing the imager strand to hybridize to the docking strand, displacing the blocker strand; and
   (e) determining whether the target-recognizing antibody has bound to the target.

2. The method of claim 1, wherein the imager strand hybridizes over a first region, but not over its full length to a second blocker strand.

3. The method of claim 2, wherein in step (d), the first blocker strand and the second blocker strand hybridize to each other.

4. The method of claim 3, wherein in step (d), the first blocker strand and the second blocker strand hybridize to each other over their entire length.

5. The method of claim 1, wherein a bouncer strand is employed to displace the imager strand, and the bouncer strand is a universal bouncer strand capable of hybridizing to all of the docking strands if multiple targets are being imaged.

6. The method of claim 1, wherein a bouncer strand is employed to displace the imager strand, and the bouncer strand is a universal bouncer strand capable of hybridizing to all of the imager strands if multiple targets are being imaged.

7. A method for imaging of at least one target in a sample comprising:
   (a) providing at least one target-recognizing antibody bound to a docking strand;
   (b) providing a first blocker strand that hybridizes to the docking strand over a first region, but not over its full length;
   (c) providing an imager strand hybridized to a second blocker strand over a first region, but not over its full length, wherein the imager strand is labeled with a detectable label;
   (d) allowing the imager strand to hybridize to at least in the region of the docking strand that does not hybridize to the first blocker strand, displacing the first blocker strand, wherein the first blocker strand and the second blocker strand hybridize to each other over their entire length; and
   (e) determining whether the target-recognizing antibody has bound to the target.

* * * * *